United States Patent

Maurer et al.

Patent Number: 5,254,081
Date of Patent: Oct. 19, 1993

[54] MULTIPLE SITE DRUG IONTOPHORESIS ELECTRONIC DEVICE AND METHOD

[75] Inventors: Donald D. Maurer, Anoka; Thomas J. Williams, Oak Grove; Scott A. Stevens, Minneapolis, all of Minn.

[73] Assignee: Empi, Inc., St. Paul, Minn.

[21] Appl. No.: 649,495

[22] Filed: Feb. 1, 1991

[51] Int. Cl.$^5$ ............................................. A61N 1/30
[52] U.S. Cl. ........................................ 604/20; 607/148; 607/149; 128/898
[58] Field of Search ............ 128/783, 798, 799, 802, 128/803, 898, 419 R, 419 B, 420, 420 A, 420.5, 421; 604/20, 49; 364/413.27

[56] References Cited

U.S. PATENT DOCUMENTS

| | | | |
|---|---|---|---|
| 4,164,226 | 8/1979 | Tapper | 128/419 |
| 4,340,047 | 7/1982 | Tapper et al. | 128/207 |
| 4,374,524 | 2/1983 | Hudek et al. | 128/420 A |
| 4,406,658 | 9/1983 | Lattin et al. | 604/20 |
| 4,457,748 | 7/1984 | Lattin et al. | 604/20 |
| 4,635,641 | 1/1987 | Hoffman | 128/639 |
| 4,729,377 | 3/1988 | Granek et al. | 128/799 |
| 4,763,660 | 8/1988 | Kroll et al. | 128/640 |
| 4,767,402 | 8/1988 | Kost et al. | 604/22 |
| 4,786,277 | 11/1988 | Powers et al. | 604/20 |
| 4,808,152 | 2/1989 | Sibalis | 604/20 |
| 4,822,334 | 4/1989 | Tapper | 128/419 R |
| 4,931,046 | 6/1990 | Newman | 604/20 |
| 4,973,303 | 11/1990 | Johnson et al. | 604/20 |
| 5,010,896 | 4/1991 | Westbrook | 128/803 |
| 5,041,974 | 8/1991 | Walker et al. | 364/413.27 |
| 5,053,001 | 10/1991 | Reller et al. | 404/20 |
| 5,058,605 | 10/1991 | Slovak | 128/783 |

FOREIGN PATENT DOCUMENTS 2111832 7/1983 United Kingdom ................ 128/799

OTHER PUBLICATIONS

Life-Tech, Inc., Publication entitled "Meditrode Iontophoresis Electrode System", May 1989, one sheet (two-sided).

Primary Examiner—C. Fred Rosenbaum
Assistant Examiner—Michael Rafa
Attorney, Agent, or Firm—Kinney & Lange

[57] ABSTRACT

A multiple site drug iontophoresis electronic device configured for controlling infusion of ionic drugs into a patient through a plurality of electrode pairs. The device includes a plurality of electrode driver channels wherein each driver channel includes an electrode output configured for electrical connection to at least one of the plurality of electrode pairs through lead wires. Each driver channel is electrically isolated from the other driver channels and includes an independent current sink which controls current intensity through the electrode output. A common controller operates the driver channels as a function of treatment parameters supplied by the patient.

32 Claims, 7 Drawing Sheets

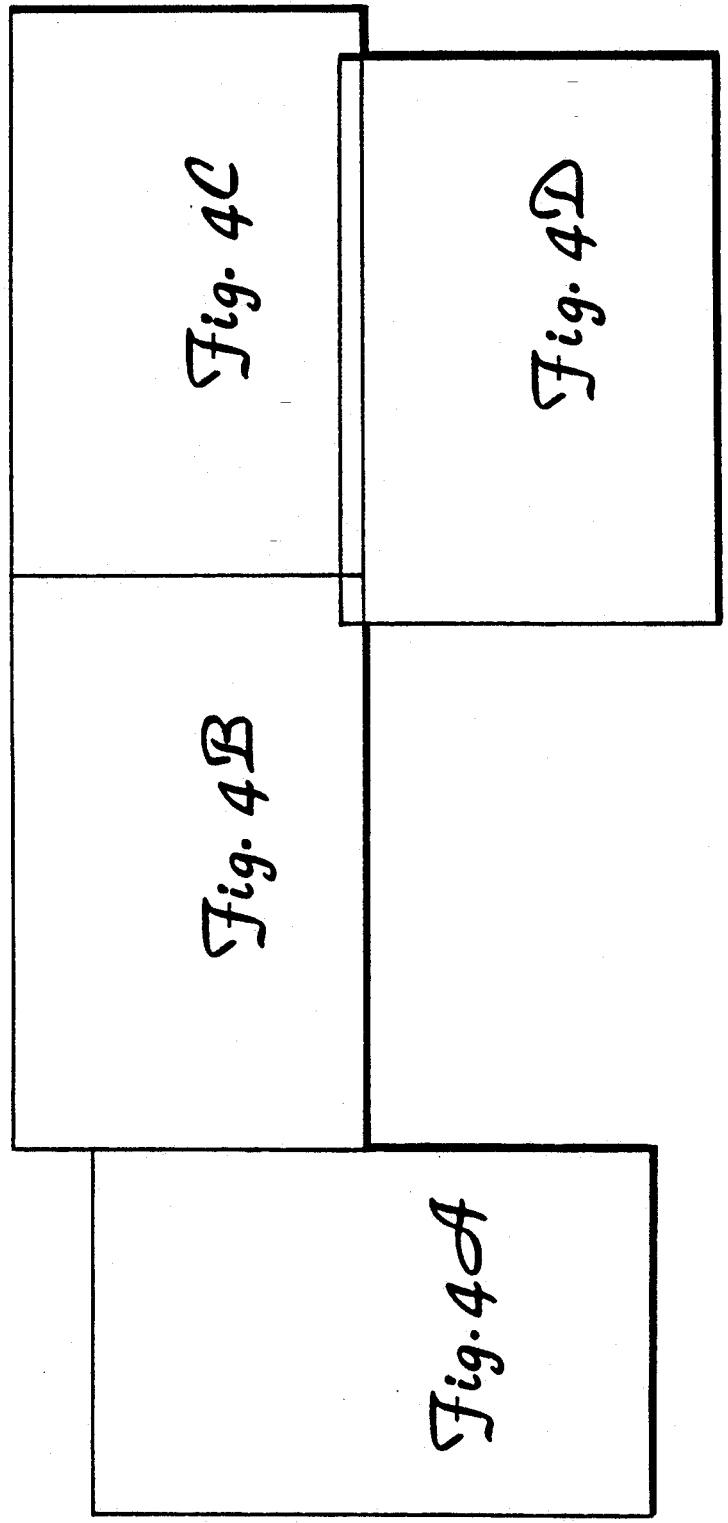

MULTIPLE SITE DRUG IONTOPHORESIS ELECTRONIC DEVICE AND METHOD

BACKGROUND OF THE INVENTION

The present invention relates to an electronic device for the infusion of ionic drugs in medical iontophoresis. In particular, the present invention relates to a multiple site iontophoresis electronic device which is capable of driving a plurality of electrodes with a single controller.

There is an ongoing search for methods of medical treatment which are noninvasive and painless. An effective treatment is useless if the patient refuses it due to the pain it can cause. Iontophoresis medication delivery systems are safe, effective, noninvasive and relatively painless.

Iontophoresis involves the interaction between ionized molecules of a drug and an external electric field, resulting in the migration of charged molecules. The migration is achieved by placing two electrodes on the patient's skin which are connected to an electric DC power supply. One of the electrodes is a source or "active" electrode filled with a drug solution. The other electrode is a return or "inactive" electrode filled with an electrolyte solution. The electric field generated between the two electrodes causes the charged drug molecules to migrate from the active electrode into the tissues and blood stream of the patient without the necessity of hypodermic injection and its adverse effects, such as pain and risk of infection. Iontophoresis tends to diffuse the drug throughout the treated tissue whereas an injection amasses a concentrated bolus of drug within the tissue or joint, potentially causing damage to the tissue.

There are two major disadvantages of iontophoresis. The first is skin irritation from acid-base concentrations created by electrolysis of the solution. The second is the slowness of drug delivery through the electrode.

Skin irritation can be reduced by chemically buffering within the electrode the H+ions produced by electrolysis. This method is disclosed in Johnson U.S. Pat. No. 4,973,303, for example. Skin irritation can also be decreased by reducing the current intensity through the electrode, or by activating the electrode for short periods, followed by rest periods.

One attempt to reduce dosage delivery time includes the use of a bifurcated lead wire connected between a single channel electrode driver circuit and two pair of electrodes with a common return. The bifurcated lead wire poses a problem. A human, transcutaneous load can vary from one hundred ohm to twelve thousand ohms, depending upon the location of the electrodes on the patient's skin. Since the driving current is constant, it will divide according to each electrode resistance, resulting in unequal diffusion from each electrode. Even if the electrode impedance could be balanced, the single output drive must provide a current intensity of two times the current intensity required for a single electrode pair to achieve comparable results. Further, the bifurcated lead wire can only drive electrodes containing drug solutions with the same polarity. This prevents simultaneous delivery of positive and negative polarized drug solutions.

SUMMARY OF THE INVENTION

The present invention is a multiple site drug iontophoresis electronic device configured for controlling infusion of ionic drugs into a patient through a plurality of electrode pairs. The device reduces skin irritation and the treatment time required for a particular dosage. The device is also capable of simultaneous delivery of positive and negative polarized drug solutions. The device includes a plurality of electrode driver channels wherein each driver channel includes an electrode output configured for electrical connection to at least one of the plurality of electrode pairs through lead wires. Each driver channel is driven by a DC power supply and is electrically isolated from the other driver channels. Each driver channel includes an independent current sink which controls current intensity through the electrode output. A controller operates the driver channels as a function of treatment parameters supplied by the patient.

In one embodiment, an isolation transformer is connected to the controller and between each electrode driver channel and the DC power supply to electrically isolate each driver channel. Each isolation transformer includes a first winding which is electrically coupled between the controller and the DC power supply and includes a second winding which is electrically coupled to the corresponding electrode driver channel. The controller operates each electrode driver channel by generating rectangular pulses that are applied to a control terminal of a transistor which is connected in series with the first winding of the corresponding isolation transformer.

Each electrode driver channel includes a DC to DC converter, which includes the isolation transformer, for accepting the rectangular pulses and converting the battery voltage into a rectified, isolated and filtered voltage. In one embodiment, the isolation transformer is a step-up transformer which approximately quintuples the battery voltage. The rectified voltage is then doubled by a circuit formed by diode/capacitor pairs, resulting in an output voltage ten times greater than the power supply voltage.

Each driver channel further includes a precision voltage reference generator, an adjustable voltage divider, a precision floating current regulator, an electrode current intensity sensing circuit and a current feedback amplifier. The rectified, isolated and filtered voltage generated by the DC to DC converter is coupled to the precision voltage reference generator. The reference voltage generated by the precision voltage reference generator is coupled to the precision floating current regulator through the adjustable voltage divider. The current regulator forms the electrode current sink which controls the current intensity through the electrode output.

The current regulator includes an operational amplifier which is connected to the adjustable voltage divider in a voltage follower configuration such that an patient can regulate the current intensity flowing through the electrode output by tuning the adjustable voltage divider. The electrode current intensity sensing circuit includes a precision sensing resistor connected in series with the electrode output to develop a voltage representative of the electrode current intensity. The feedback amplifier transforms the representative voltage into a current that is fed back to the controller.

The controller includes a microprocessor and a timer circuit. The microprocessor and the timer circuit are commercially available integrated circuit packages. For example in an embodiment with two electrically isolated driver channels, the timer circuit includes a standard 556 dual timer. The dual timer receives a clock signal and an output enable signal from the microprocessor and delivers the rectangular pulses to the electrode driver channels. The timer reduces the duty cycle of the clock signal and delays delivery of the rectangular pulses to one driver channel with respect to the other driver channel in order to enhance battery life.

The microprocessor is responsible for providing overall timing and counting for the device and for determining output actions for the input combinations presented to it. The microprocessor includes firmware which provides means for acquiring data, making calculations and affecting appropriate operations of the device through output control and annunciation. The firmware includes a main program and several modules which are responsible for specific operations The main program calls individual modules to perform their required functions. In one embodiment the microprocessor is a one-time programmable microprocessor.

The microprocessor includes several inputs that are used by the patient to control the infusion of ionic drugs through the electrodes during the treatment period. These inputs include a treatment dosage (in milliamp-minutes), an operational mode and a display selection. The microprocessor drives a liquid crystal display that is multiplexed between several selectable parameters. In one embodiment, the parameters include elapsed time (minutes), dosage remaining (milliamp-minutes), current intensity (mA) and channel number. These parameters are selected from switches connected to the microprocessor.

The microprocessor operates in three modes; set up, pause and run. In set up mode, the patient enters a prescribed dosage in milliamp-minutes. Each channel is programmed independently. For example, in a two-channel device the patient first selects channel 1 setup and programs channel 1, then selects channel 2 setup and programs channel 2. The display provides the appropriate channel parameters during set up.

During pause mode, the microprocessor "powers up" each channel. Shunt circuitry re-routes current flow away from the electrode output of each electrode driver channel so that the current intensity can be adjusted by tuning the adjustable voltage divider before any current is delivered to the patient. The microprocessor monitors the current intensity for each electrode driver channel through the current feedback amplifiers and transmits the current information to the liquid crystal display. The user can then tune the current intensity for each channel to a predetermined level.

When the patient switches the microprocessor from pause mode to run mode, the microprocessor disables the shunt circuitry and operates each electrode driver channel to deliver the selected current intensity for a treatment period as determined from the resulting current intensity and the dosage parameters supplied by the patient.

The microprocessor monitors the current feedback signals for each electrode driver channel and maintains a total count of milliamp-minutes delivered to the patient. The microprocessor also supplies the patient with warning signals when the electrode current intensity drops below a specified level or when other various fault conditions occur. The user warning signals are applied to annunciators which give both visual and audible alerts to the patient. A light emitting diode (LED) provides the visual alert to the patient while a buzzer provides the audible alert. In one embodiment, the device includes one LED for each electrode driver channel. Therefore, the microprocessor can indicate to the patient which electrode driver channel is malfunctioning.

The device of the present invention significantly reduces the two major disadvantages of medical iontophoresis. First, the device can reduce skin irritation by electrically alternating electrode output current from each driver channel. Thus, the device continually delivers a drug dosage, but each individual electrode has a rest period during which the $H^+$ and $OH^-$ ions chemically recombine to reduce the skin irritating elements. The skin irritating elements are reduced effectively by one-half in a two-channel device. Alternatively, a two-channel device can reduce skin irritation by one-half by reducing the electrode output current by one-half while keeping the dosage and time the same. The two-channel device can deliver twice the total quantity of drugs at one-half the electrical current level as compared to a single channel device.

Second, the device of the present invention reduces drug delivery time. Two pair of electrodes deliver the drug at an infusion rate that is four times greater than a single pair of electrodes for the same parameters of time and current. Thus, for the same dosage, the time could be reduced by one-fourth, thus solving the problem of slowness of delivery.

A further advantage of the isolated, independent electrode driver channel configuration is that the drug solutions delivered by each electrode pair are not required to be of the same polarity as the drug solutions in the other electrodes. Therefore, the device of the present invention has greater versatility in drug delivery than do iontophoretic devices of the prior art.

BRIEF DESCRIPTION OF THE DRAWINGS

FIG. 4e is a block diagram which illustrates how FIGS. 4a, 4b, 4c and 4d are to be arranged.

DETAILED DESCRIPTION OF THE PREFERRED EMBODIMENTS

The present invention is a multiple-site drug iontophoresis electronic device which is capable of driving a plurality of electrodes with a single controller. The electrodes are driven by a plurality of electrically isolated electrode driver channels which have independently controlled current intensity. The device delivers twice the total quantity of drugs at one-half the electrical current level for two electrode driver channels as compared to a single driver channel. This may be extended to N channels, where the required current to deliver N times the total drug dosage would be the single channel current divided by N. Practical considerations of design limit N to less than ten. The following description and the figures are directed toward one preferred embodiment in which the device includes two electrode driver channels.

Figure 1:
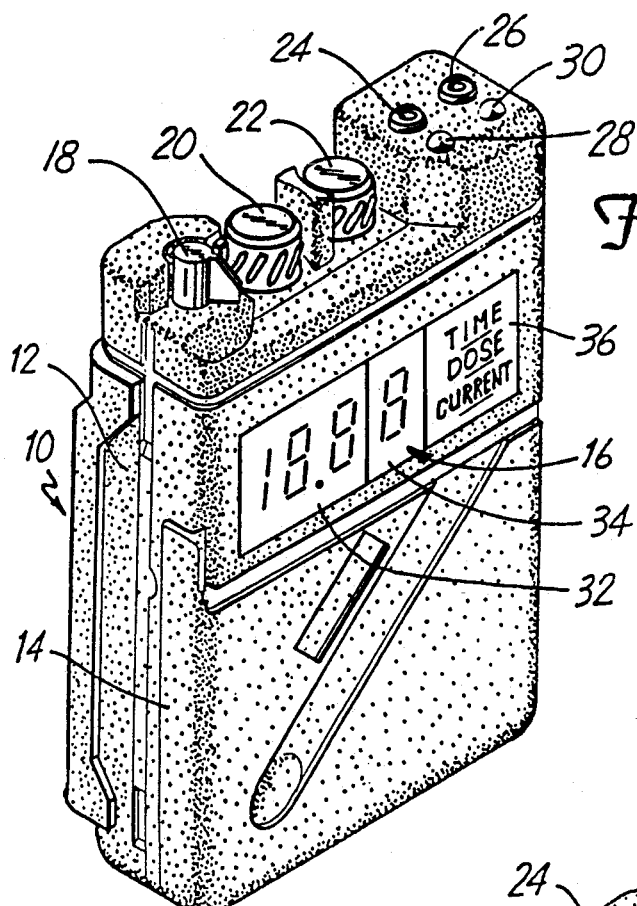
FIG. 1 is a perspective view of a multiple site drug iontophoresis electronic device, in accordance with the present invention.

FIG. 1 is a perspective view of multiple site drug iontophoresis electronic device 10 in accordance with the present invention. Device 10 includes housing 12, flip-cover 14, LCD display 16, treatment control switch 18, dose increment switch 20, dose decrement switch 22, electrode output jacks 24 and 26 and light emitting diodes 28 and 30.

Iontophoresis device 10 is connected to a patient through one or two pair of electrodes (not shown). One of the electrodes in each pair is a source or "active" electrode filled with a drug solution. The other electrode in each pair is a return or "inactive" electrode filled with an electrolyte solution. Each pair of electrodes is connected to iontophoresis device 10 through lead wires coupled to a plug which is inserted into either electrode output jack 24 or 26. Jacks 24 and 26 each include tip and sleeve contacts for connection to the plug. Current flow through electrode output jacks 24 and 26 generates an electric field between the active and inactive electrodes which causes the charged drug molecules to migrate from the active electrode into the tissues and blood stream of the patient.

LCD display 16 displays useful parameters to the patient. In the embodiment shown, LCD display 16 is a 4.5 digit floating point liquid crystal display. Although display 16 is shown as a liquid crystal display, any suitable display can be used with the present invention. LCD display 16 is divided into sections 32, 34 and 36. Section 32 displays elapsed time (min), dosage remaining (mA×min), and current (mA). Section 34 displays the corresponding channel number. Section 36 displays which parameter (time, dose or current) is being displayed in section 32. These parameters may be selected from switches located beneath the flip-cover 14.

Treatment control switch 18 selects from four operational modes. These modes include setup channel 1, setup channel 2, pause and run. The setup modes allow each channel to be programmed independently. In setup mode, the patient selects the dose display on LCD display 16 using switch 48 and enters a prescribed dose in milliamp-minutes by depressing dose increment switch 20 to increase the dosage and dose decrement switch 22 to decrease the dosage. In one embodiment switches 20 and 22 are momentary contact push button switches.

In pause mode, device 10 "powers-up" each electrode driver channel. Device 10 includes shunt circuitry (shown in FIG. 4c) that re-routes current flow away from electrode output jacks 24 and 26 so that the patient can adjust the current intensity in each channel through a 1KΩ sense resistor while monitoring the current intensity on LCD display 16, without delivering any current through the output jacks.

When the patient moves treatment control switch 18 from pause mode to run mode, device 10 disables the shunt circuitry and operates each electrode driver channel to deliver current through output jacks 24 and 26 for a treatment period as determined by the dosage parameters supplied by the patient and the resulting current intensity.

Iontophoresis device 10 supplies the patient with warning signals when the electrode current intensity in either channel 1 or channel 2 drops below a specified level, or when various other fault conditions occur. The user warning signals are applied to annunciators which give both visual and audible alerts to the patient. LEDs 28 and 30 provide the visual alert to the patient while a buzzer (not shown) provides the audible alert. LED 28 provides the visual alert to the patient of fault conditions occurring in channel 1 and in the electrode pair connected to jack 24. LED 30 provides the visual alert to the patient of fault conditions occurring in channel 2 and in the electrode pair connected to jack 26.

Figure 2:
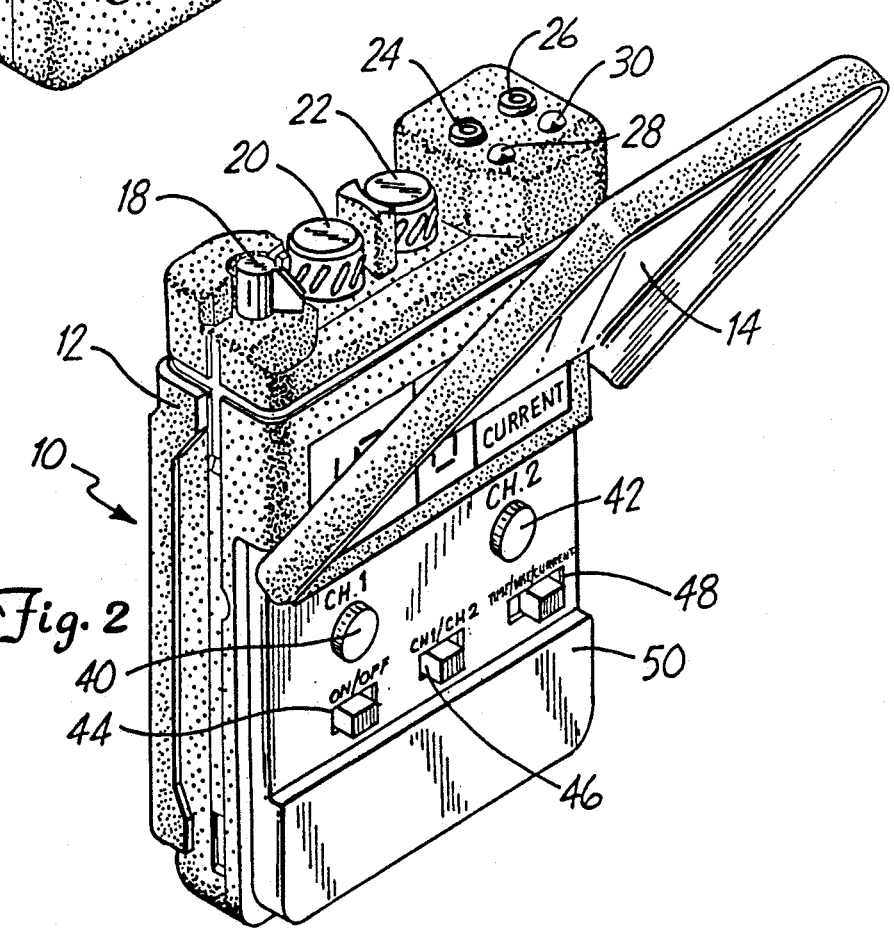
FIG. 2 is a perspective view of the device of FIG. 1 with a flip-cover raised to expose additional treatment and display controls.

FIG. 2 is a perspective view of iontophoresis device 10 with flip-cover 14 raised to expose channel 1 current intensity knob 40, channel 2 current intensity knob 42, power switch 44, channel select switch 46 and parameter select switch 48. The position of channel select switch 46 determines which channel is currently displayed on LCD display 16. The position of parameter select switch 48 determines whether time, dose or current is displayed on LCD display 16. Channel 1 current intensity knob 40 can be adjusted to tune the current intensity delivered by electrode driver channel 1 through output jack 24. Channel 2 current intensity knob 42 can be adjusted in a similar manner to tune the current intensity delivered by electrode driver channel 2 through output jack 26. The current intensity can be adjusted in either pause mode or run mode. In one embodiment, iontophoresis device 10 includes a 9-volt battery (not shown) that supplies power to the electrical components that form the device. The 9-volt battery is positioned within battery compartment 50 which is accessed from the rear of housing 12, opposite flip-cover 14.

Figure 3:
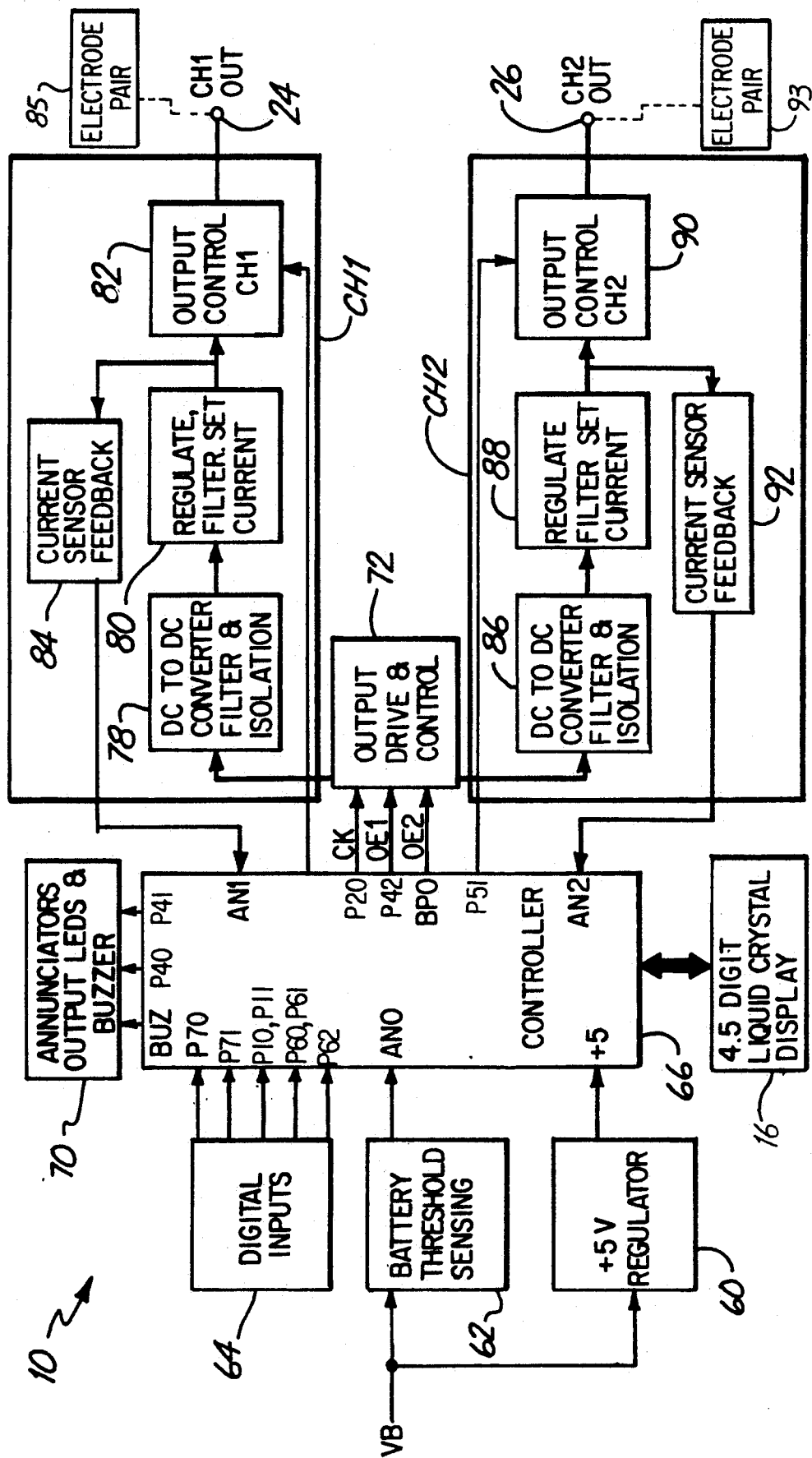
FIG. 3 is a block diagram of the multiple site drug iontophoresis electronic device shown in FIG. 1.

FIG. 3 is a block diagram of iontophoresis device 10. Iontophoresis device 10 includes 5-volt regulator block 60, battery threshold sensing block 62, digital input block 64, controller 66, 4.5 digit LCD display 16, annunciator block 70, output driver and control block 72, and electrode driver channels CH1 and CH2. As shown in greater detail in FIGS. 4a, 4b, 4c and 4d, each block in FIG. 3 is connected to battery voltage terminal VB and is powered by the battery voltage or by a 5-volt regulated voltage generated by 5-volt regulator block 60. For clarity, these connections are not shown in FIG. 3.

Electrode driver channels CH1 and CH2 are electrically isolated from each other and include an independent current sink which controls current intensity through its associated electrode output jack 24 or 26. Controller 66 operates driver channels CH1 and CH2 as functions of treatment parameters supplied by the patient to deliver the selected current level to the patient through electrode outputs 24 and 26 for the treatment period.

Controller 66 provides timing and counting for operation of the overall system and determines output actions for the input combinations presented to it. Output drive, timing and control block 72 receives clock signals CK and output enables OE1 and OE2 from controller 66 and delivers electrical control signals to electrode driver channels CH1 and CH2. Controller 66 can either enable or disable electrode driver channel CH1 through output enable OE1. Similarly, controller 66 can either enable or disable electrode driver channel CH2 through output enable OE2.

Electrode driver channel CH1 includes DC-to-DC converter, filter and isolation block 78, regulator, filter and output current set block 80, output control block 82, current sensor feedback block 84, and electrode output jack 24. Jack 24 is connected to electrode pair 85. Similarly, electrode output driver channel CH2 includes DC-to-DC converter, filter and isolation block 86, regulator, filter and output current set block 88, output control block 90, current sensor feedback block 92 and electrode output jack 26. Jack 26 is connected to electrode pair 93. Because electrode driver channels CH1 and CH2 are identical, the following discussion is primarily limited to electrode driver channel CH1.

In response to the electrical control signals received from output drive, timing and control block 72, block 78 modulates the battery voltage and converts the modulated voltage to a rectified, isolated and filtered voltage that is input to the regulator, filter and output current set block 80. Block 80 delivers the electrode output current when driven by output drive, timing and control block 72. Output control block 82 allows controller 66 to measure the electrode output current intensity without affecting the patient and provides a shunt path away from output jack 24 for the electrode output current if pause mode is selected.

Current sensor feedback block 84 senses the electrode output current and feeds back that value continuously to analog input AN1 of controller 66 where it can be processed. Controller 66 monitors and integrates the current feedback signals and updates treatment status values such as elapsed time and dosage delivered.

Figure 4A:
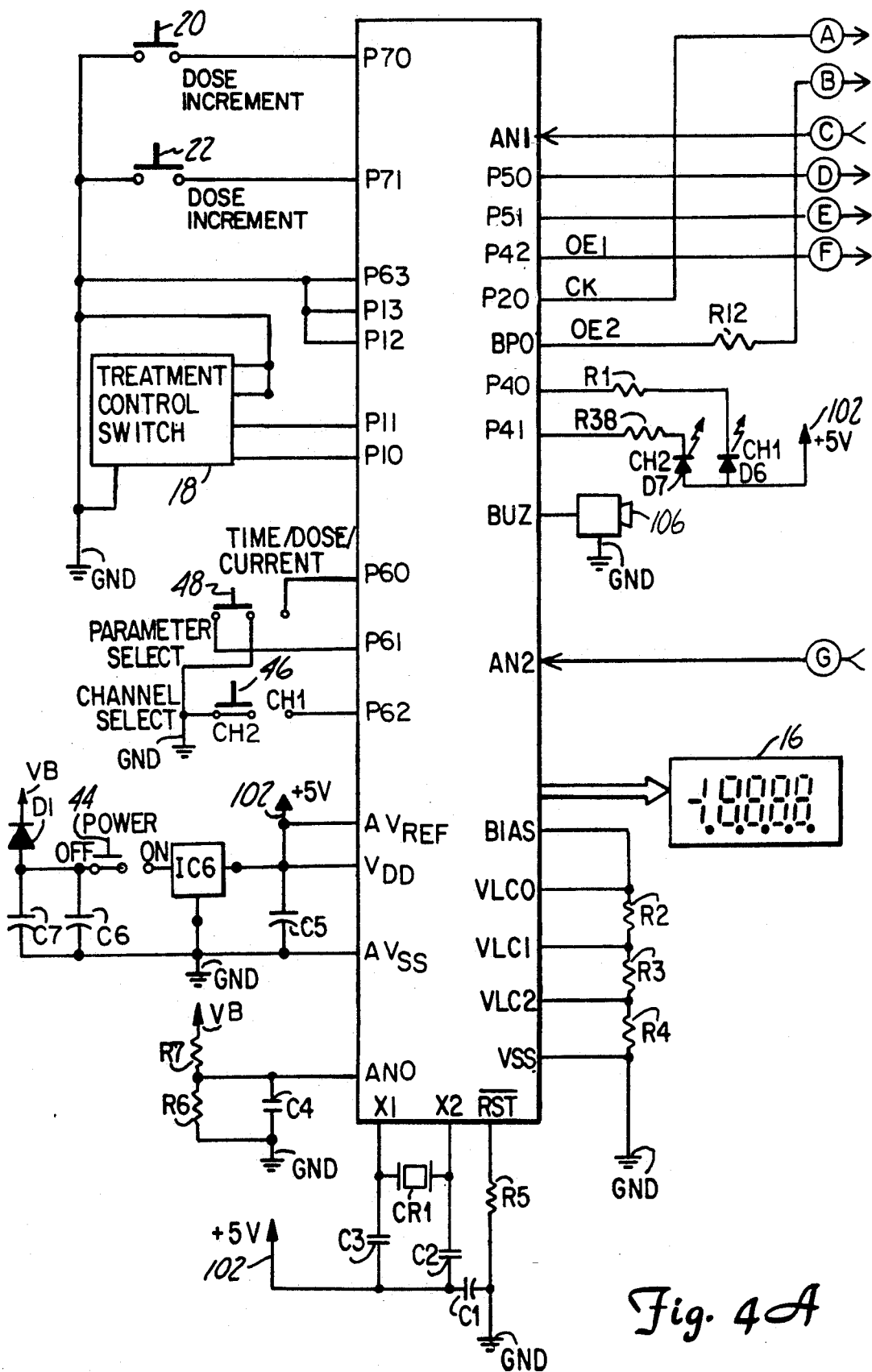
FIGS. 4a, 4b, 4c and 4d together form a detailed schematic diagram of the multiple site drug iontophoresis electronic device shown in FIGS. 1 through 3.
Figure 4B:
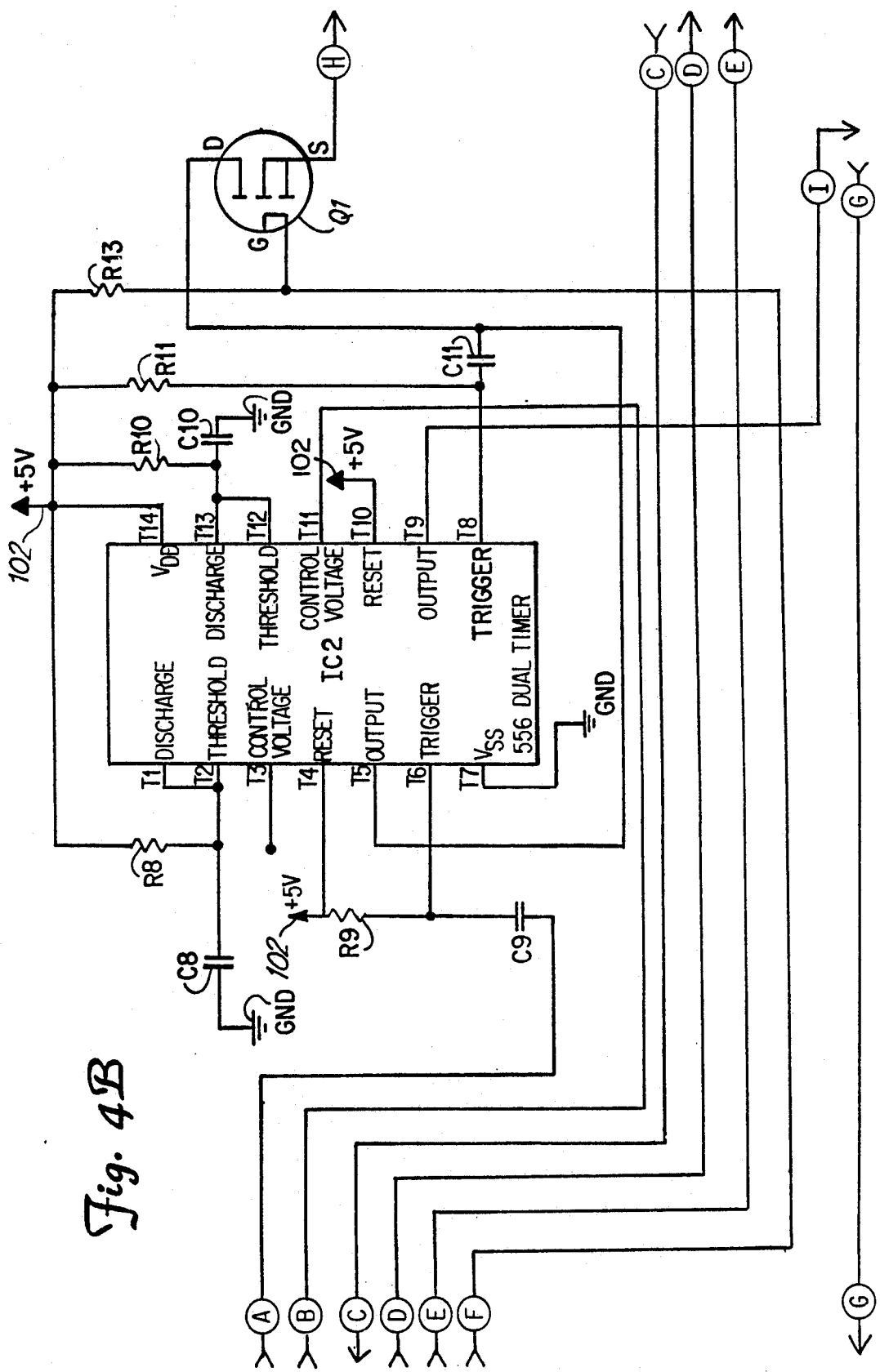
Figure 4C:
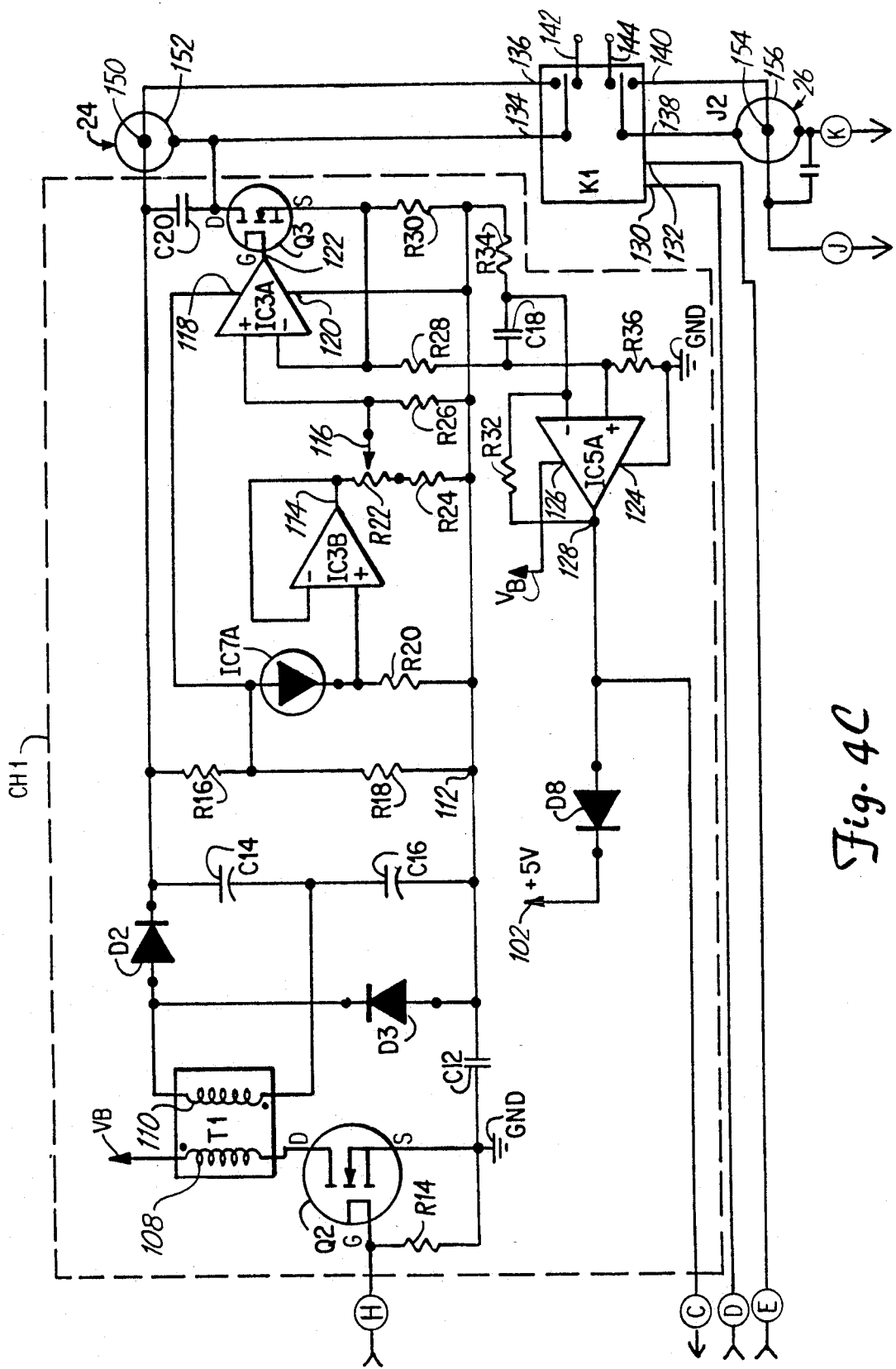
Figure 4D:
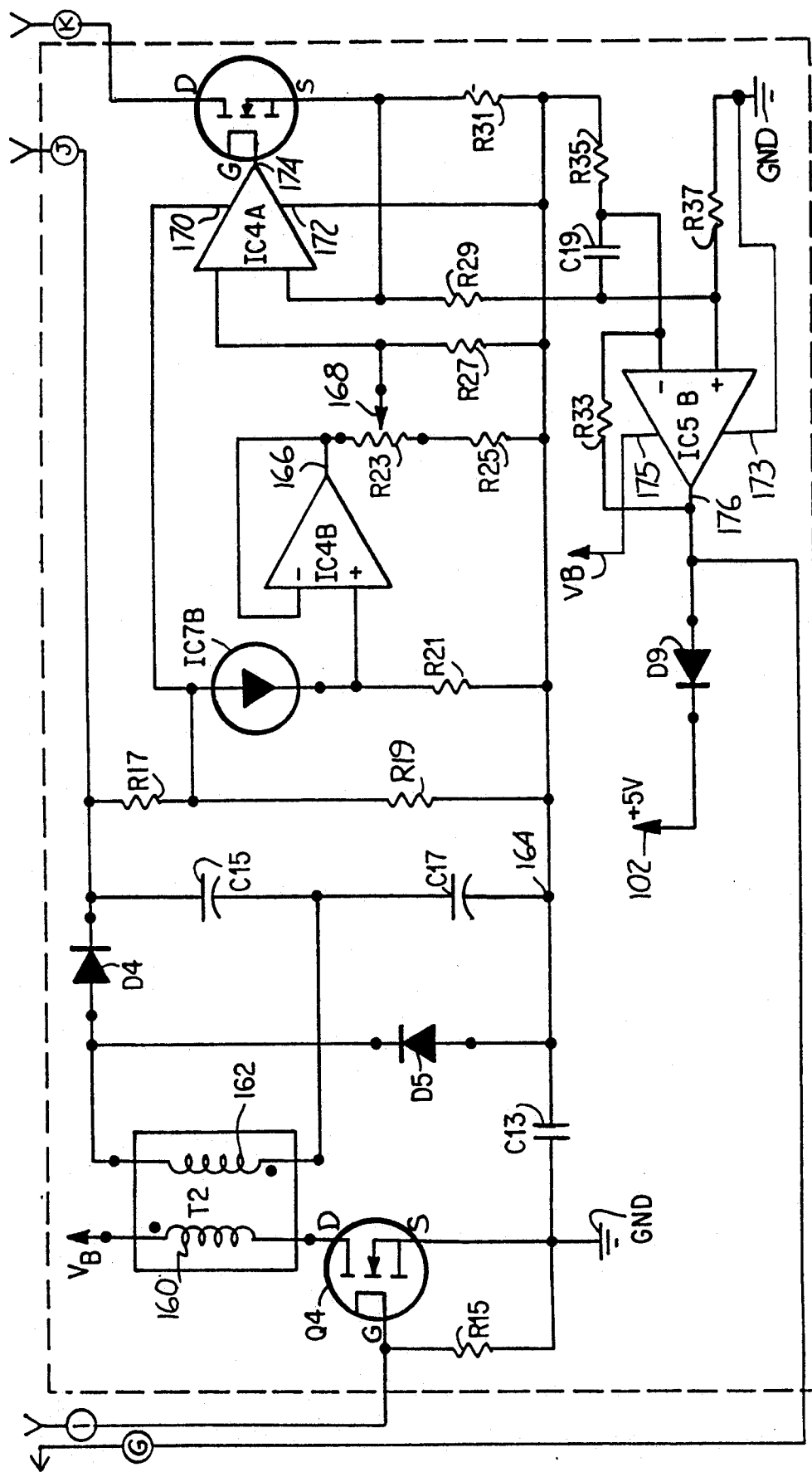

FIGS. 4a, 4b, 4c and 4d together form a detailed schematic diagram of iontophoresis device 10 shown in FIGS. 1–3. FIG. 4e is a block diagram which illustrates how FIGS. 4a, 4b, 4c and 4d are to be arranged. FIGS. 4a and 4b are arranged side by side. FIG. 4c is arranged to the right of FIG. 4b. FIG. 4d is arranged below FIG. 4c. The following discussion makes reference to both FIGS. 3 and 4. Controller 66 (shown in FIG. 3) includes microprocessor IC1. Microprocessor IC1 can include any suitable, commercially available microprocessor. In one embodiment, microprocessor IC1 is a one-time programmable microprocessor, such as an NEC 75P328PG, that is programmed with firmware to provide means for acquiring data, making calculations, and affecting appropriate operations of the device through output control and annunciation. The firmware includes a primary program and several modules which are individually responsible for specific operations. The primary program summons individual modules to perform their required functions.

Battery threshold sensing block 62 (shown in FIG. 3) includes resistors R6 and R7 and capacitor C4. Precision resistors R6 and R7 are connected in series between battery terminal VB and ground terminal GND. The 9-volt battery (not shown) is connected between battery terminal VB and ground terminal GND. Capacitor C4 is connected in parallel across resistor R6. Analog input pin AN0 of microprocessor IC1 is connected to a node between resistors R6 and R7. Microprocessor IC1 measures the battery voltage by monitoring the voltage level at analog input pin AN0. Clock signal CK generated by microprocessor IC1 on output pin P20 is discretely pulse-width modulated.

5-volt regulator block 60 includes diode D1, capacitors C5, C6 and C7, power switch 44 and integrated circuit IC6. The anode of diode D1 is connected to battery terminal VB and the cathode is connected to a first terminal of power switch 44. Capacitors C6 and C7 are connected together in parallel between the first terminal of power switch 44 and ground terminal GND. Integrated circuit IC6 is a low-power voltage regulator that supplies a regulated power source to 5-volt regulated terminal 102 and to microprocessor IC1 at input pins AVref and Vdd. Integrated circuit IC6 is connected between a second terminal of power switch 44, input pins AVss and Vdd of microprocessor IC1 and ground terminal GND. Capacitor C5 is connected between input pins AVss and Vdd of microprocessor IC1.

Digital input block 64 (shown in FIG. 3) includes treatment control switch 18, dose increment switch 20, dose decrement switch 22, channel select switch 46 and parameter select switch 48. Treatment control switch 18 is connected between ground terminal GND and input pins P10 and P11 of microprocessor IC1. As discussed with reference to FIG. 1, treatment control switch 18 drives iontophoresis device 10 between setup channel 1, setup channel 2, pause and run modes.

Dose increment switch 20 is connected between ground terminal GND and input pin P70 of microprocessor IC1. Dose decrement switch 22 is connected between ground terminal GND and input pin P71 of microprocessor IC1. Dose increment and dose decrement switches 20 and 22 are momentary contact push button switches.

Channel select switch 46 is connected between ground terminal GND and input pin P62 of microprocessor IC1. The position of channel select switch 46 determines which channel CH1 or CH2 is displayed on LCD display 16 and can be adjusted in dosage by the patient. Parameter select switch 48 is connected between ground terminal GND and input pins P60 and P61 of microprocessor IC1. The position of parameter select switch 48 determines which of the treatment parameters time, dose or current are displayed on LCD display 16.

Microprocessor IC1 is driven by a crystal oscillator circuit formed by crystal CR1, capacitors C1, C2 and C3 and resistor R5. Crystal CR1 is connected between input pins X1 and X2 of microprocessor IC1. Capacitor C3 is connected between input pin X1 and 5-volt regulated terminal 102. Capacitor C2 is connected between input pin X2 and 5-volt regulated terminal 102. Capacitor C1 is connected between 5-volt regulated terminal 102 and ground terminal GND. Resistor R5 is connected between ground terminal GND and active-low input pin RST. The crystal oscillator circuit forms the primary timing of microprocessor IC1 from which clock signals CK are generated at output pin P20 of microprocessor IC1.

The duty cycle of clock signals CK are increased as the battery voltage level decreases. This enables device 10 to sink current into the highest specified human, transcutaneous loads as the battery reaches the end of its life.

Resistors R2, R3 and R4 are connected in series between output pin BIAS and ground terminal GND to form a voltage divider circuit that biases microprocessor input pins VLC0, VLC1, VLC2. Microprocessor output pin BIAS provides a voltage level to the voltage divider circuit. Pin Vss is connected to ground terminal GND. Pin VLC2 is connected to the node between resistors R3 and R4. Pin VLC1 is connected to the node between resistors R2 and R3. Finally, pin VLC0 is connected to output pin BIAS.

Liquid crystal display 16 is connected to microprocessor IC1 through display bus 104. Display bus 104 is a 15-bit bus that transmits control signals to the LCD display to produce the desired display characters.

Annunciator block 70 (shown in FIG. 3) includes buzzer 106, light emitting diodes D6 and D7, and resistors R1 and R38. Buzzer 106 is connected between microprocessor output pin BUZ and ground terminal GND. The anodes of light emitting diodes D6 and D7 are connected at 5-volt regulated terminal 102. Resistor R1 is connected between microprocessor output pin P40 and the cathode of light emitting diode D6. Resistor R38 is connected between microprocessor output pin P41 and the cathode of light emitting diode D7. Microprocessor IC1 generates user warning signals that are applied to output pins P40, P41 and BUZ which give both visual and audible alerts to the patient. Light emitting diode D6 provides the visual alert to the patient with respect to electrode driver channel CH1 while light emitting diode D7 provides the visual alert with respect to electrode driver channel CH2. Buzzer 106 provides the audible alert to the patient with respect to both electrode driver channels CH1 and CH2. Microprocessor IC1 supplies the patient with warning signals when the electrode current intensity in electrode driver channel CH1 or CH2 drops below a specified level, or when various other fault conditions occur.

Output drive and control block 72 includes integrated circuit IC2, resistors R8, R9, R10, R11, R12 and R13, capacitors C8, C9, C10 and C11, and transistor Q1. In the embodiment shown in FIG. 4, integrated circuit IC2 includes a 556 dual timer with a first timer circuit and a second timer circuit. However, any other suitable timing circuit can be used with the present invention. The first timer circuit includes discharge pin T1, threshold pin T2, control voltage pin T3, reset pin T4, output pin T5 and trigger pin T6. The second timer circuit includes output pin T9, reset pin T10, control voltage pin T11, threshold pin T12 and discharge pin T13. Integrated circuit IC2 further includes power supply pin Vss (pin T7) which is connected to ground terminal GND and power supply pin Vdd (pin T14) which is connected to 5-volt regulated terminal 102.

Capacitor C8 is connected between ground terminal GND and a common connection between discharge pin T1 and threshold pin T2. Resistor R8 is connected between 5-volt regulated terminal 102 and the common connection between discharge pin T1 and threshold pin T2. Control voltage pin T3 is not connected. Reset pin T4 is connected to 5-volt regulated terminal 102. Resistor R9 is connected between reset pin T4 and trigger pin T6. Capacitor C9 is connected between trigger pin T6 and microprocessor output pin P20. Capacitor C11 is connected between output pin T5 and trigger pin T8. Output pin T5 is connected to the drain terminal of transistor Q1. Power supply pin Vss (pin T7) is connected to ground terminal GND. Output pin T9 is connected to the gate terminal of transistor Q4. Reset pin T10 is connected to 5-volt regulated terminal 102. Resistor R12 is connected between control voltage pin T11 and microprocessor output pin BP0. Capacitor C10 is connected between ground terminal GND and a common connection between threshold pin T12 and discharge pin T13. Resistor R10 is connected between capacitor C10 and 5-volt regulated terminal 102. Resistor R11 is connected between trigger pin T8 and 5-volt regulated terminal 102. Resistor R13 is connected between 5-volt regulated terminal 102 and the gate terminal of transistor Q1. The gate terminal of transistor Q1 is connected to microprocessor output pin P42. Power supply pin Vdd (pin T14) is connected to 5-volt regulated terminal 102.

Integrated circuit IC2 receives clock signals CK from microprocessor output pin P20 and delivers rectangular pulses to electrode driver channels CH1 and CH2 through output pins T5 and T9, respectively. Integrated circuit IC2 delays delivery of the rectangular pulses to electrode output channel CH2 in order to enhance battery life. Electrode driver channels CH1 and CH2 are therefore staggered and operate in synchrony with clock signals CK. The values of resistors R8, R10 and capacitors C8, C10 set the duty cycle of the rectangular pulses.

Output pin T5 of the first timer circuit is fed into trigger input pin T8 of the second timer circuit through capacitor C11 such that the first timer circuit drives the second timer circuit. This configuration provides the delay between the pulses on output pins T5 and T9 for electrode driver channels CH1 and CH2, respectively.

The rectangular pulses produced at output pin T5 are applied to the drain terminal of transistor Q1. Output enable signal OE1 produced at microprocessor output pin P42 is applied to the gate terminal of transistor Q1 to gate the rectangular pulses through transistor Q1. When output enable OE1 is high, transistor Q1 turns on and allows the rectangular pulses to reach electrode driver channel CH1 at the gate terminal of transistor Q2.

The rectangular pulses produced at output pin T9 are applied to electrode driver channel CH2 at the gate terminal of transistor Q4. Output enable OE2 is applied to control voltage input pin T11 of integrated circuit IC2 to enable and disable the second timer circuit, and therefore control the application of the rectangular pulses to electrode driver channel CH2.

DC-to-DC converter, filter and isolation block 78 (shown in FIG. 3) includes resistor R14, step-up transformer T1, transistor Q2, diodes D2 and D3, and capacitors C12, C14 and C16. The gate or "control" terminal of transistor Q2 is connected to the source terminal of transistor Q1. The source terminal of transistor Q2 is connected to ground terminal GND. Resistor R14 is connected between the gate terminal and source terminal of transistor Q2. Step-up transformer T1 is an isolation transformer and includes primary winding 108 and secondary winding 110. Primary winding 108 is connected between battery voltage terminal VB and the drain terminal of transistor Q2. The drain and source terminals of transistor Q2 form a primary flow path in series with primary winding 108. The gate terminal of transistor Q2 controls the flow of current through primary winding 108.

A first terminal of secondary winding 110 is connected to the anode of diode D2 and to the cathode of diode D3. Capacitor C14 is connected between the cathode of diode D2 and a second terminal of secondary winding 110. Capacitor C16 is connected between the second terminal of secondary winding 110 and the anode of diode D3. Capacitor C12 is connected between the anode of diode D3 and ground terminal GND.

The rectangular pulses are applied to the gate terminal of a transistor 92 to modulate the battery voltage at battery voltage terminal VB through primary winding 108. DC to DC converter, filter and isolation block 78 converts the modulated battery voltage (6-9VDC) to a rectified, isolated and filtered voltage (60-90VDC) that is applied to the regulator, filter and output current set block 80. Step-up transformer T1 approximately quintuples the battery voltage across primary winding 108. This voltage is then doubled by diode/capacitor pairs D2, D3/C14, C16. The resulting 10×voltage multiplication factor also reduces the current through secondary winding 110 by the same amount. The efficiency of DC to DC converter, filter and isolation block 78 is ninety percent or better, due primarily to low loss core material in step-up transformer T1. The configuration of DC to DC converter, filter and isolation block 78 provides approximately 1.5 meg ohms of interchannel isolation.

The rectified, isolated and filtered voltage is applied to the regulator, filter and output current set block 80 (shown in FIG. 3). Block 80 includes resistors R16, R18, R20, R24 and R26, potentiometer R22, precision current source IC7A, operational amplifiers IC3A and IC3B, and transistor Q3. Resistors R16 and R18 are connected in series between the cathode of diode D2 and node 112. Precision current source IC7A is connected between the node between resistors R16 and R18 and the noninverting input to operational amplifier IC3B. Resistor R20 is connected between the noninverting input of operational amplifier IC3B and node 112. Operational amplifier IC3B is connected in a voltage follower configuration with its output 114 connected to its inverting input. Potentiometer R22 and resistor R24 are connected in series between operational amplifier output 114 and node 112. Resistor R26 is connected between tap 116 of potentiometer R22 and node 112. Tap 116 is connected to the noninverting input of operational amplifier IC3A. Positive supply terminal 118 of operational amplifier IC3A is connected to the node between resistors R16 and R18. Negative supply terminal 120 of operational amplifier IC3A is connected to node 112. Output 122 of operational amplifier IC3A is connected to the gate terminal of transistor Q3.

Regulator, filter and output current set block 80 maintains electrode output current through transistor Q3 about a set level from 1 to 4 mA DC. Precision current source IC7A and operational amplifier IC3B form a precision voltage reference generator and buffer that present a full-scale 4-volt reference voltage at output 114. Potentiometer R22 and resistor R24 form an adjustable voltage divider network that divides the reference voltage. The divided voltage at tap 116 is applied to the noninverting input of operational amplifier IC3A. Potentiometer R22 is adjusted by the patient through channel 1 current intensity knob 40 (shown in FIG. 2) to tune the divided voltage at the noninverting input of amplifier IC3A and thus the current intensity through output jack 24.

Operational amplifier IC3A and transistor Q3 form a floating current regulator or "current sink". The current regulator is floating since positive supply terminal 118 floats, and is only biased by resistors R16 and R18. Bias resistors R16 and R18 also provide a discharge path for capacitors C14 and C16 such that there is no possible residual charge. The floating current regulator configuration is advantageous since the bias point of the current regulator may be designed such that the allowable range of battery voltage is extended without exceeding the operating limits of either precision current source IC7A (4-40VDC) or operational amplifiers IC3A and IC3B (6-36VDC). Operational amplifier IC3A is connected in a voltage follower configuration that drives a voltage on sense resistor R30 that is equal to the divided reference voltage at its noninverting input.

Electrode output jack 24 includes tip 150 and sleeve 152. Tip 150 is connected to the cathode of diode D2 while the sleeve 152 is connected to the drain terminal of transistor Q3. Filter capacitor C20 is connected between tip 150 and sleeve 152 of jack 24. Electrode output jack 24 provides the output for electrode driver channel CH1.

The overall efficiency of blocks 78 and 80 (shown in FIG. 3) is sixty-three percent to eighty-five percent, where higher efficiencies are achieved when delivering larger electrode output currents rather than smaller. There are two sources for current regulator error. The first source is the gate leakage current in transistor Q3 which is on the order of nanoamperes and is very small in comparison to the current it regulates. The second source of error is the input offset voltage of operational amplifier IC3A, which is approximately 0.15 mV. Resistor R30 is connected in series with electrode output jack 24. If resistor R30 has a value of 1KΩ (which is similar to a human, transcutaneous load), 0.15 mV offset voltage represents only 0.15 microamperes of error current. Therefore, these two error currents combined account for 0.005 percent regulation error over the specified load range.

Current sensor feedback block 84 (shown in FIG. 3) includes resistors R28, R30, R32, R34 and R36, capacitor C18, diode D8 and feedback amplifier IC5A. Resistor R28 is connected between the source terminal of transistor Q3 and the noninverting input terminal of feedback amplifier IC5A. Resistor R30 is connected between the source terminal of transistor Q3 and node 112. Resistor R34 is connected between node 112 and the inverting input terminal of feedback amplifier IC5A. Capacitor C18 is connected between the inverting and noninverting input terminals of feedback amplifier IC5A. Resistor R36 is connected between the noninverting input of feedback amplifier IC5A and ground terminal GND.

Feedback amplifier IC5A includes negative supply terminal 124, positive supply terminal 126 and output 128. Negative supply terminal 124 is connected to ground terminal GND. Positive supply terminal 126 is connected to battery voltage terminal VB. Resistor R34 is connected between the inverting input of feedback amplifier IC5A and output 128 of feedback amplifier IC5A. The anode of diode D8 is connected to output 128.

The cathode of diode D8 is connected to 5-volt regulated terminal 102. Output 128 of feedback amplifier IC5A is connected to analog input terminal AN1 of microprocessor IC1.

Current sensor feedback block 84 (shown in FIG. 3) senses the electrode output current flowing through transistor Q3 and continuously supplies current feedback signals to microprocessor analog input AN1 where the signals can be processed. Resistor R30 forms a precision current sense resistor with a tolerance of 0.1 percent. Sense resistor R30 develops a voltage drop that is proportional to the electrode output current flowing through transistor Q3. Feedback amplifier IC5A converts the voltage drop across resistor R3 to a current that forms the feedback signals at output 128. Diode D8 is a clamping diode that protects the microprocessor analog input AN1.

Output control block 82 (shown in FIG. 3) includes magnetically controlled latch K1. Latch K1 is common to both output control blocks 82 and 90 and includes control inputs 130 and 132 and outputs 134, 136, 138, 140, 142 and 144 Control inputs 130 and 132 are connected to microprocessor output pins P50 and P51. Latch K1 is connected across the output of electrode driver channel CH1 at jack 24. Output 134 is connected to sleeve 152 and output 136 is connected to tip 150.

Latch K1 is also connected across the output of electrode driver channel CH2 at jack 26. Jack 26 includes tip 154 and sleeve 156. Filter capacitor C21 is connected between tip 154 and sleeve 156. Latch output 138 is connected to sleeve 156 and latch output 140 is connected to tip 154. Latch outputs 142 and 144 are not connected.

Latch K1 provides shunt paths for the electrode output currents of both output jacks 24 and 26 when pause mode is selected. When pause mode is selected, microprocessor IC1 provides a pause signal on either output pin P50 or P51. The pause mode signal causes latch K1 to short outputs 134 and 136 together and outputs 138 and 140 together. This shunts the electrode output currents from both output jacks 24 and 26. The shunt paths allow the patient to power-up each electrode driver channel CH1 and CH2 during pause mode to adjust and monitor the electrode output current intensity without affecting the attached electrodes. The shunt paths also provide a safety feature that can be used to shunt the electrode output currents if a fault condition occurs in the system. Further, if the battery voltage level falls below a specified level, resulting in a low electrode output current intensity, such as 0.9 mA, microprocessor IC1 enters pause mode, shunts the electrode current outputs with latch K1 and suspends the treatment session. Once the battery is replaced, the patient can move treatment control switch 18 back into run mode to continue the treatment session. Microprocessor IC1 saves the treatment parameters while the batteries are being replaced.

Electrode driver channel CH2 is identical to electrode driver chancel CH1. Therefore, the following discussion is limited to a recitation of the component parts of electrode driver channel CH2 and their interconnections. DC to DC converter, filter and isolation block 86 (shown in FIG. 3) includes resistor R15, transistor Q4, step-up transformer T2, diodes D4 and D5 and capacitors C13, C15 and C17. Resistor R15 is connected between the gate terminal of transistor Q4 and ground terminal GND. The source terminal of transistor Q4 is connected to ground terminal GND. Step-up transformer T2 includes a primary winding 160 and a secondary winding 162. Primary winding 160 is connected between battery voltage terminal VB and the drain terminal of transistor Q4. A first terminal of secondary winding 162 is connected to the anode of diode D4 and to the cathode of diode D5. Capacitor C15 is connected between the cathode of diode D4 and a second terminal of secondary winding 162. Capacitor C17 is connected between the second terminal of secondary winding 162 and node 164. The anode of diode D5 is connected to node 164. Capacitor C13 is connected between node 164 and ground terminal GND.

Regulator, filter and output current set block 88 (shown in FIG. 3) includes bias resistors R17, R19, R21, R25 and R27, potentiometer R23, precision current source IC7B, operational amplifiers IC4A and IC4B, and transistor Q5. Bias resistors R17 and R19 are connected in series between the cathode of diode D4 and node 164. Precision current source IC7B is connected between the node between resistors R17 and R19 and the noninverting input of operational amplifier IC4B. Resistor R21 is connected between the noninverting input terminal of operational amplifier IC4B and node 164. Output 166 of operational amplifier IC4B is connected to the inverting input terminal of operational amplifier IC4B. Potentiometer R23 is connected between output 166 and resistor R25. Resistor R25 is connected between potentiometer R23 and node 164. Potentiometer R23 includes tap 168 which is connected to the noninverting input of operational amplifier IC4A. Resistor R27 is connected between tap 168 and node 164. Tap 168 is tuned by the patient through channel 2 current intensity knob 42 (shown in FIG. 2).

Operational amplifier IC4A includes positive supply terminal 170, negative supply terminal 172 and output terminal 174. Positive supply terminal 170 is connected to the node between bias resistors R17 and R19. Negative supply voltage terminal 172 is connected to node 164. Output terminal 174 is connected to the gate terminal of transistor Q5. The drain terminal of transistor Q5 is connected to sleeve 156 of electrode output jack 26. The source terminal of transistor Q5 is connected to the inverting input of operational amplifier IC4A and to current sense resistor R31.

Current sensor feedback block 92 (shown in FIG. 3) includes electrode output current sense resistor R31, bridge resistors R29, R33, R35 and R37, capacitor C19, feedback amplifier IC5B and diode D9. Sense resistor R31 is connected between the source terminal of transistor Q5 and node 164. Bridge resistor R29 is connected between the source terminal of transistor Q5 and the noninverting input of feedback amplifier IC5B. Resistor R35 is connected between resistor R31 at node 164 and the inverting input of feedback amplifier IC5B. Capacitor C19 is connected between the inverting and noninverting inputs of feedback amplifier IC5B. Resistor R37 is connected between the noninverting input of feedback amplifier IC5B and ground terminal GND. Negative supply terminal 173 is connected to ground terminal GND. Positive supply terminal 175 is connected to battery voltage terminal VB. Resistor R33 is connected between the inverting input of feedback amplifier IC5B and output 176 of feedback amplifier IC5B. Output 176 is connected to the anode of diode D9. The cathode of diode D9 is connected to 5-volt regulated terminal 102. Output 176 is connected to analog input AN2 of microprocessor IC1.

Current sensor feedback block 92 provides feedback signals to analog input AN2 that are representative of the electrode output current flowing through transistor Q5 of electrode driver channel CH2. Microprocessor IC1 monitors the feedback signals at analog inputs AN1 and AN2 and integrates or "meters" these signals to maintain a running total of the dosage in milliamp-minutes delivered to the patient during run mode. During pause mode, the feedback signals are monitored by microprocessor IC1 and can be displayed on LCD display 16 to facilitate adjustment by the patient of the electrode output current intensity to suggested levels before treatment begins.

CONCLUSION

Medical iontophoresis involves the interaction between ionized molecules of a drug solution and an external electric field, resulting in the migration of charged molecules. The migration is achieved by placing a pair of electrodes on the patient's skin which are connected to either electrode driver channel CH1 or CH2 at jacks 24 or 26, respectively. The electrode output current drives charged molecules within the drug solution of the same polarity into the tissue. The delivered dosage has a simple dependence on current level and application time (current $\times$ time = dose).

The multiple site drug iontophoresis electronic device of the present invention significantly reduces skin irritation from acid-base concentrations caused by electrolysis of the drug solution and significantly reduces the drug delivery treatment time. By adding an additional electrode driver channel to an iontophoresis device which is electrically isolated and independently controlled in current intensity, the device is able to deliver twice the total concentration of a drug at one-half of the intensity. For example with a single channel device, given a drug infusion rate of 1 ugm/mA min at an electrode current intensity of 3 mA for 10 min, the quantity of drug delivered will be:

$$3 mA \times 10\ min \times 1\ \mu gm/mA\ min = 30\ \mu gm \quad (1)$$

If the electrode has an area of 8 cm², the drug tissue density will be:

$$30 \mu g/m/8\ cm^2 = 3.75\ \mu gm/cm^2 \quad (2)$$

In a two-channel device, the 8 cm² electrode can be divided into two electrically independent electrode pairs with one pair being driven by electrode driver channel CH1 and the other pair being driven by electrode driver channel CH2. If each electrode has an area of 4 cm² with the same level of current intensity applied for the same amount of time, the device achieves a drug infusion rate that is four times that of a single 8 cm² electrode pair. This result is shown in the following equation:

$$\frac{3\ mA \times 10\ min \times 1\ ugm/mA\ min}{4\ cm^2} = 7.5\ ugm/cm^2 \quad \text{EQUATION 3}$$

Therefore, the overall drug infusion rate of both electrode pairs is:

$$2 \times 7.5\ \mu gm/cm^2 = 15\ \mu gm/cm^2 \quad (4)$$

$$\frac{15\ ugm/cm^2}{3.75\ ugm/cm^2} = 4 \quad \text{EQUATION 5}$$

Thus, the two electrically independent electrode pairs deliver at an infusion rate that is 4 times for the same parameters of time and current as a single electrode pair.

As a result, a patient could reduce the electrode output current to 1.5 mA and proportionately reduce the skin irritation factor while maintaining the same dosage without increasing treatment time. Alternatively, microprocessor IC1 can operate the electrode driver channels CH1 and CH2 to electrically alternate output from each channel so that the device continuously delivers a drug dosage, with each electrode having a rest period during which the H+ and OH− ions chemically recombine, effectively reducing the skin irritation elements effectively by one-half.

With a drug infusion rate that is four times greater for the same parameters of time and current than a single electrode, the patient can deliver the same dosage in one-fourth the time or 2.5 minutes, thus solving the problem of slow delivery.

Another advantage of the present invention is that the device is capable of simultaneous delivery of positive and negative polarized drug solutions. This capability greatly enhances the versatility of the electronic device as two different drug treatments can be delivered at the same time. It is even possible to simultaneously administer treatment to two separate patients with independent control of each treatment using the same device.

Although the present invention has been described with reference to preferred embodiments, workers skilled in the art will recognize that changes may be made in form and detail without departing from the spirit and scope of the invention.

What is claimed is:

1. An electronic, iontophoresis controller for controlling infusion of ionic drugs into a patient, the controller comprising:

a plurality of iontophoresis source and return electrodes configured for attachment to the patient's skin, wherein each source electrode contains the ionic drugs and creates an electrical current path through the patient with at least one corresponding return electrode for transcutaneously delivering the ionic drugs into the patient;

controller means for controlling operation of the iontophoresis source and return electrodes; and a plurality of iontophoresis electrode driver channels wherein each channel includes:

an iontophoresis electrode output configured for electrical connection to at least one source electrode and at least one corresponding return electrode;

an independent direct-current regulator which generates a direct-current output at a selected direct-current intensity through the electrode output; and isolation means coupled to the electrode output and the independent current regulator for electrically isolating each electrode output from the electrode outputs of the other driver channels and for electrically isolating the controller means from the electrode outputs of at least one driver channel, 2. The electronic iontophoresis controller of claim 1 wherein the isolation means comprises a plurality of isolation transformers with each transformer corresponding to an electrode driver channel and having a first winding electrically coupled to the controller means and a second winding electrically coupled to the corresponding electrode driver channel.

3. The electronic, iontophoresis controller of claim 2 and further comprising:

a voltage supply terminal connected to the first winding;

a ground terminal; and a transistor including first and second terminals forming a primary current flow path connected in series between the first winding and the ground terminal, and including a control terminal connected to the controller means for modulating a voltage at the voltage supply terminal through the first winding.

4. The electronic, iontophoresis controller of claim 3 wherein each electrode driver channel comprises direct-current to direct-current converter means for accepting electrical signals from the controller means and converting the modulated voltage into a rectified, isolated and filtered voltage.

5. The electronic, iontophoresis controller of claim 4 wherein the direct-current to direct-current converter means comprises the isolation transformer.

6. The electronic, iontophoresis controller of claim 4 wherein each electrode driver channel further comprises a precision voltage reference generator which is electrically coupled to the direct-current to direct-current converter means to receive the rectified, isolated and filtered voltage and to generate a precision reference voltage.

7. The electronic, iontophoresis controller of claim 1 wherein each electrode driver channel further comprises:
a precision voltage reference generator electrically coupled to the isolation means for generating a precision reference voltage; and
an adjustable voltage divider coupled between the precision voltage reference generator and the current regulator means to divide the precision reference voltage, whereby an operator can tune the adjustable voltage divider to regulate the selected direct-current intensity of the direct-current output with the current regulator means.

8. The electronic, iontophoresis controller of claim 7 wherein the current regulator means comprises a floating current regulator having a feedback amplifier connected to the adjustable voltage divider in a voltage follower configuration such that the electrode current intensity is representative of the voltage divider adjustment.

9. The electronic, iontophoresis controller of claim 1 wherein each electrode driver channel further includes an electrode current intensity sensing circuit which is connected in series with the electrode output to sense the direct-current output generated by the direct-current regulator.

10. The electronic, iontophoresis controller of claim 9 wherein the electrode current intensity sensing circuit includes a precision sensing resistor that develops a voltage drop which is proportional to the direct-current output.

11. The electronic, iontophoresis controller of claim 9 wherein each electrode driver channel further includes current feedback means electrically connected between the electrode current intensity sensing circuit and the controller means for providing feedback signals to the controller means which are representative of the direct-current output.

12. The electronic, iontophoresis controller of claim 11 and further comprising annunciator means electrically connected to the controller means for receiving user warning signals generated by the controller means as a function of the feedback signals and for transmitting the warning signals to the patient.

13. The electronic, iontophoresis controller of claim 12 wherein the annunciator means includes a light emitting diode which provides to the patient visual output of the user warning signals.

14. The electronic, iontophoresis controller of claim 12 wherein the annunciator means includes an electronic buzzer which provides to the patient aural output of the user warning signals.

15. The electronic, iontophoresis controller of claim 11 and further comprising display means electrically connected to the controller means for receiving treatment parameters generated by the controller means which are representative of the direct-current output and for displaying the parameters to the patient.

16. The electronic, iontophoresis controller of claim 11 and further comprising:
shunt means driven between open and closed states by the controller means and electrically connected across each electrode output such that the shunt means shunts current across the electrode outputs when in the closed state and allows current to flow through the electrode output when in the open state; and
wherein the shunt means is configured to allow current to flow through the electrode current intensity sensing circuit in both the open and closed states.

17. The electronic, iontophoresis controller of claim 11 wherein the controller means comprises:
means for entering treatment parameters by the patient to control the infusion of the ionic drugs into the patient; and
a microprocessor connected to the means for entering treatment parameters and having electrode driver enable outputs which selectively enable individual electrode driver channels as functions of the treatment parameters.

18. The electronic, iontophoresis controller of claim 17 wherein the microprocessor further comprises a clock output and wherein the control means further comprises timer means which is connected to the clock output and the electrode driver enable outputs for producing electrode driver signals which operate the plurality of electrode driver channels to control the flow of current at the electrode outputs.

19. The electronic, iontophoresis controller of claim 18 wherein the timer means is configured to alternate the electrode driver signals between the plurality of electrode driver channels.

20. An electric, iontophoresis controller configured for connection to a plurality of iontophoresis electrode pairs for controlling infusion of ionic drugs into a patient through the electrode pairs, the controller comprising:
a plurality of electrode driver channels wherein each channel includes:
an electrode output configured for electrical connection to at least one of the electrode pairs;
an independent direct-current regulator which generates a direct-current output at a selected current intensity through the electrode output;
direct-current to direct-current converter means for accepting electrical signals from the controller means;
a precision voltage reference generator which is electrically coupled to the direct-current to direct-current converter means to generate a precision reference voltage; and
isolation means coupled to the electrode output and the independent current regulator for electrically isolating each driver channel from the other driver channels; and
controller means for controlling operation of the electrode driver channels, wherein the controller means is coupled to the plurality of electrode driver channels such that the isolation means isolates the controller means from the electrode output.

21. A method of delivering precision direct-current into a human, transcutaneous load for medical iontophoresis, the method comprising:
attaching a plurality of iontophoresis source and return electrodes to the human, transcutaneous load such that each source electrode creates an electrical current path through the load with at least one of the corresponding return electrodes;
providing a plurality of electrically isolated electrode driver channels wherein each channel comprises an electrode output and an independent direct-current regulator which generates a direct-current output at a selected direct-current intensity through the electrode output;

coupling the electrode output to the independent direct-current regulator;

coupling each electrode driver channel to at least one of the iontophoresis source electrodes and corresponding return electrodes; and operating the plurality of electrode driver channels with a common controller to deliver precision direct current through the human, transcutaneous load for a treatment period.

22. The method of claim 21 and further comprising the step of metering the direct-current output delivered to the human, transcutaneous load through each electrode driver circuit with the common controller.

23. The method of claim 22 wherein the step of operating the common controller comprises:
powering up each electrode driver channel;
shunting the precision direct current away from the electrode output;
metering the intensity of the precision direct current; and
adjusting the current intensity to a selected level 24. The method of claim 21 wherein the step of operating the plurality of electrode driver channels comprises entering a selected dosage into the common controller for each electrode driver channel.

25. The method of claim 21 wherein the step of providing a plurality of electrically isolated electrode driver channels comprises providing an isolation transformer between the common controller and each electrode output.

26. The method of claim 25 wherein the step of operating the plurality of electrode driver channels comprises:
generating electrode control signals with the common controller as a function of treatment parameters supplied to the controller by a user;
selectively applying the electrode control signals to a first winding of each isolation transformer;
converting electrical signals, produced by a second winding of each isolation transformer in response to the electrode control signals, into a precision voltage reference;
applying the precision voltage reference to an adjustable current regulator which forms the current regulator, and
tuning the adjustable current regulator to achieve a selected current intensity through the electrode output.

27. The method of claim 25 wherein the step of operating the plurality of electrode driver channels to deliver the precision direct current for a treatment period comprises:
generating electrode control signals with the common controller as a function of treatment parameters supplied to the common controller by a user;
selectively applying the electrode control signals to each isolation transformer; and
alternating between each electrode driver channel when performing the step of selectively applying the electrode control signals.

28. The method of claim 21 wherein the step of operating the plurality of electrode driver channels to deliver the precision direct current for a treatment period further comprises:

operating N electrode driver channels for a dosage treatment period at a direct current of 1/N times a dosage current.

29. The method of claim 21 wherein the step of operating the plurality of electrode driver channels to deliver the precision direct current for a treatment period further comprises:
operating N electrode driver channels at a dosage current for a treatment period of 1/N times a dosage treatment period.

30. The method of claim 21 wherein:
the step of attaching a plurality of source and return electrodes includes attaching first and second electrode pairs to the human, transcutaneous load;
the step of providing a plurality of electrically isolated electrode driver channels includes providing first and second electrically isolated electrode driver channels;
the step of coupling each electrode driver channel includes coupling the first electrode driver channel to the first electrode pair and the second electrode driver channel to the second electrode pair; and
the step of operating the electrode driver channels includes operating the first electrode driver channel to deliver precision direct-current with a first polarity and operating the second electrode driver channel to deliver precision direct-current with a second polarity, opposite the first polarity.

31. A method of simultaneous delivery of positive and negative polarized drug solutions through a human, transcutaneous load, the method comprising:
attaching a first source electrode and a first return electrode to the human, transcutaneous load, with the first source electrode containing a positively polarized drug solution;
attaching a second source electrode and a second return electrode to the human, transcutaneous load, with the second source electrode containing a negatively polarized drug solution;
providing first and second electrically isolated electrode driver channels wherein each channel comprises an electrode output and an independent direct-current regulator which is coupled to the electrode output and generates a direct-current output at a selected current intensity through the electrode output;
coupling the electrode output of the first electrode driver channel to the first source and return electrodes and coupling the electrode output of the second electrode driver channel to the second source and return electrodes; and
operating the first and second electrode driver channels with a common controller to deliver precision direct current with a first polarity through the electrode output of the first electrode driver channel and to deliver precision direct current with a second polarity, opposite the first polarity, through the electrode output of the second electrode driver channel.

32. A method of delivering precision direct-current into a human, transcutaneous load, the method comprising:
attaching a plurality of electrode pairs to the human, transcutaneous load;
providing a plurality of electrically isolated electrode driver channels wherein each channel comprises an electrode output and an independent direct-current current regulator which generates a direct-current output at a selected current intensity through the electrode output;
coupling the electrode output to the independent direct-current regulator;
coupling each electrode driver channel to at least one of the plurality of electrode pairs;

powering up each electrode driver channel;
shunting the precision direct-current away from the electrode output;
metering an intensity of the precision direct-current; and
adjusting the current intensity to a selected level.

* * * * *

UNITED STATES PATENT AND TRADEMARK OFFICE
CERTIFICATE OF CORRECTION

PATENT NO. : 5,254,081

DATED : October 19, 1993

INVENTOR(S) : DONALD D. MAURER, THOMAS J. WILLIAMS, SCOTT A. STEVENS

It is certified that error appears in the above-identified patent and that said Letters Patent is hereby corrected as shown below:

Col. 16, line 38, delete "electronic iontophoresis", insert --electronic, iontophoresis--

Signed and Sealed this

Twelfth Day of April, 1994

Attest:

BRUCE LEHMAN

*Attesting Officer*  *Commissioner of Patents and Trademarks*